United States Patent
Aponte et al.

(10) Patent No.: US 11,288,834 B2
(45) Date of Patent: Mar. 29, 2022

(54) DETERMINING THE RELATIVE POSITION BETWEEN A POINT CLOUD GENERATING CAMERA AND ANOTHER CAMERA

(71) Applicant: Brainlab AG, Munich (DE)

(72) Inventors: Pablo Aponte, Haar (DE); Jochen Veigel, Rosenheim (DE); Ivana Ivanovska, Aschheim (DE); Hagen Kaiser, Icking (DE)

(73) Assignee: BRAINLAB AG, Munich (DE)

( * ) Notice: Subject to any disclaimer, the term of this patent is extended or adjusted under 35 U.S.C. 154(b) by 29 days.

(21) Appl. No.: 16/075,450

(22) PCT Filed: May 23, 2017

(86) PCT No.: PCT/EP2017/062384
§ 371 (c)(1),
(2) Date: Aug. 3, 2018

(87) PCT Pub. No.: WO2018/215053
PCT Pub. Date: Nov. 29, 2018

(65) Prior Publication Data
US 2021/0209750 A1    Jul. 8, 2021

(51) Int. Cl.
*G06T 7/73* (2017.01)
*G06T 7/586* (2017.01)
(Continued)

(52) U.S. Cl.
CPC ............. *G06T 7/73* (2017.01); *G06T 7/0012* (2013.01); *G06T 7/557* (2017.01); *G06T 7/586* (2017.01);
(Continued)

(58) Field of Classification Search
None
See application file for complete search history.

(56) References Cited

U.S. PATENT DOCUMENTS 9,436,993 B1 * 9/2016 Stolka .................... A61B 5/742
2013/0010079 A1    1/2013 Zhang et al.
(Continued)

FOREIGN PATENT DOCUMENTS

EP              1563799 A1    8/2005
WO    WO-2013104420 A1 *  7/2013    ............. G01S 5/163

OTHER PUBLICATIONS

Jaramillo, et al. "6DOF Pose Localization in 3D Point-Cloud Dense Maps Using a Monocular Camera" Proceedings of the IEEE International Conference on Robotics and Biomimetics. Dec. 2013. (Year: 2013).*

(Continued)

*Primary Examiner* — Vu Le
*Assistant Examiner* — Courtney Joan Nelson
(74) *Attorney, Agent, or Firm* — Middleton Reutlinger

(57) ABSTRACT

A method for determining the relative position between a first camera and a second camera used in a medical application, wherein the first camera captures a 2D image of a phantom, the second camera emits light onto the phantom and analyzes the reflected light, thus generating a 3D point cloud representing points on the surface of the phantom, and the phantom has a planar surface forming a background on which a plurality of 2D markers are formed, wherein one of the background and the 2D markers is reflective, thus reflecting light emitted by the second camera back to the second camera, and the other one is non-reflective, thus not reflecting light emitted by the second camera back to the second camera, the method involving that a) the first camera captures a 2D image of the phantom, b) the second camera generates a 3D point cloud representing the planar surface of the phantom, c) the 2D markers are identified in the 2D image, thus obtaining 2D marker data representing the locations of the 2D markers in the 2D image, d) the 2D (Continued)

markers are identified in the 3D point cloud using the property that points on a non-reflective part of the planar surface are identified as having a larger distance to the second camera than points on a reflective part of the planar surface, thus obtaining 3D marker data representing the locations of the 2D markers in a reference system of the second camera, and e) finding the relative position between the first camera and the second camera by applying a Perspective-n-Points algorithm on the 2D marker data and the 3D marker data.

16 Claims, 5 Drawing Sheets

(51) Int. Cl.
 *G06T 7/557* (2017.01)
 *G16H 30/40* (2018.01)
 *G06T 7/00* (2017.01)
(52) U.S. Cl.
 CPC ... *G16H 30/40* (2018.01); *G06T 2207/10028* (2013.01); *G06T 2207/30244* (2013.01)

(56) References Cited

U.S. PATENT DOCUMENTS

| | | | |
|---|---|---|---|
| 2014/0336461 A1* | 11/2014 | Reiter | A61B 1/06 600/111 |
| 2015/0145966 A1* | 5/2015 | Krieger | H04N 13/122 348/47 |
| 2016/0012588 A1 | 1/2016 | Taguchi et al. | |
| 2016/0364867 A1* | 12/2016 | Moteki | G06T 7/73 |

OTHER PUBLICATIONS

International Search Report and Written Opinion issued in Application No. PCT/EP2017/062384 dated May 23, 2017.
Krishnan, et al. "Cross-Calibration of RGB and Thermal Cameras with a LIDAR" IROS Workshop on Alternative Sensing for Robot Perception. 2015.
Ababsa, et al. "Robust Camera Pose Estimation Using 2D Fiducials Tracking for Real-Time Augmented Reality Systems" Virtual Reality Continuum and its Applications Proceedings of the 2004 ACM Siggraph International Conference on Virtual Reality Continuum and its Applications in Industry. Jan. 1, 2004.
Jaramillo, et al. "6DoF Pose Localization in 3D Point-Cloud Dense Maps Using a Monocular Camera" Proceedings of the IEEE International Conference on Robotics and Biomimetics. Dec. 2013.

* cited by examiner

DETERMINING THE RELATIVE POSITION BETWEEN A POINT CLOUD GENERATING CAMERA AND ANOTHER CAMERA

TECHNICAL FIELD

The present invention relates to a computer implemented method for determining the relative position between a first camera and a second camera and to a corresponding computer program and system.

SUMMARY

There are scenarios in medical applications in which two different cameras are used. The first camera can be any camera, such as a camera generating 2D images, like 2D RGB images. The second camera generates a 3D point cloud, such as a Time-of-Flight (ToF) or a structured light camera, by emitting light onto an object and analyzing the reflected light. It might then be necessary to know or determine the calibration between the two cameras. The calibration means the relative position between the two cameras and is also referred to as a set of extrinsic parameters. Contrary to that, intrinsic parameters of a camera describe how incoming radiation, such as light, is processed, for example using an optical system, and converted into an electrical output signal. The intrinsic parameters for example describe the focal length and aberrations introduced by a camera.

In this document, the term "position" means a combination of an orientation given in up to three rotational dimensions and a location given in up to three translational dimensions.

In the present invention, the calibration between the cameras is determined by imaging a phantom using both cameras and analyzing the output data of the two cameras. The phantom has particular properties such that markers located on the phantom cannot only be recognized in the output image of the first camera, but also in the 3D point cloud output by the second camera.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The present invention relates to a method for determining the relative position between a first camera and a second camera used in a medical application. The first camera captures a 2D image of a phantom. The phantom is a particular object used in the present invention. The 2D image represents incident radiation, for example in the visible and/or infrared spectrum. It shall be noted that the first camera can for example also be a stereoscopic camera, which captures two 2D images. The first camera can be a thermographic camera which generates a thermal image of incident infrared radiation.

The second camera emits light onto the phantom and analyzes the reflected light, thus generating a 3D point cloud representing points on the surface of the phantom. The second camera is, for example, a Time-of-Flight (ToF) camera or a structured light camera. A ToF camera measures the time required by a light signal to travel to the phantom and back to the camera. In this document, the expression ToF camera comprises any suitable LiDAR (light detection and ranging) apparatus. A structured light camera projects known light patterns onto the phantom and analyzes the reflected light to create the 3D point cloud.

The phantom has a planar surface forming a background on which a plurality of 2D markers are formed, wherein one of the background and the markers is reflective, thus reflecting light emitted by the second camera back to the second camera, and the other one is non-reflective, thus not reflecting light emitted by the second camera back to the second camera. In other words, the planar surface has either reflective markers on a non-reflective background or non-reflective markers on a reflective background.

In this document, a surface is considered to be reflective if it reflects a certain amount of the incoming light energy back to the second camera, such as at least 20%, 25%, 30%, 50%, 75% or 90%. A surface is considered to be non-reflective if the amount of light energy reflected back to the second camera is below a predetermined threshold, such as 15%, 10%, 5%, 3%, 2% or 1%. A non-reflective surface can for example absorb (most of) the incident light or reflect the incident light into a direction other than the direction in which the second camera is located. The property, that is reflective or not, preferably only applies to the wavelengths used by the second camera to generate the 3D point cloud. This means that a non-reflective surface is allowed to reflect non-used wavelengths back to the second camera and a reflective surface is allowed to not reflect non-used wavelengths back to the second camera.

The phantom can also have more than one planar surface, wherein two or more planar surfaces form a background on which 2D markers are formed. Besides the one or more planar surface(s), the phantom can have additional surfaces. A surface is considered to be planar if the distances of all points on the surface have a distance to a plane fitted through those points are below a predetermined threshold, such as an absolute threshold or a relative threshold. The absolute threshold can be, for example, 10 mm, 5 mm, 3 mm, 2 mm or 1 mm. The relative threshold can for example be a fraction of the square root of the area occupied by the surface points, such as ⅒, 1/20, 1/50, 1/75, 1/100, 1/200 or 1/250.

The method of the present invention comprises the step of capturing a 2D image of the phantom using the first camera. It further comprises the step of generating a 3D point cloud representing the planar surface of the phantom by the second camera, or more correctly representing points on the planar surface of the phantom.

The method further involves the step of identifying the 2D markers in the 2D image, thus obtaining 2D marker data representing the locations of the 2D markers in the 2D image. The location is preferably defined by two coordinates in the 2D image. The location of a marker for example means the center of the marker in the 2D image. Identifying the location of a marker is, for example, based on the known shape of the 2D marker. The shape of the 2D marker, or of its projection into the image plane of the 2D image, is identified in the 2D image. If the 2D marker is, for example, circular, the depiction of the 2D marker in the 2D image is elliptical. The location of a 2D marker in the 2D image, for example, indicates the center of mass of the 2D marker. A suitable algorithm for finding ellipses, which correspond to depictions of circular 2D markers, in the 2D image is described in the paper "Precise ellipse estimation without contour point extraction" by Ouellet et al.

The present method further involves the step of identifying the 2D markers in the 3D point cloud. This identification uses the property that points on a non-reflective part of the planar surface are identified as having a larger distance to the second camera than points on a reflective part of the planar surface. If a particular point on a non-reflective part does not reflect light back to the second camera, the distance of this point to the second camera is found to be large or even infinite. With the reflective/non-reflective properties of the 2D markers and the background as explained above, the shapes of the 2D markers can also be identified in the 3D point cloud. Identifying the 2D markers in the 3D point cloud thus obtains 3D marker data representing the locations of the 2D markers in a reference system of the second camera. The locations of the 2D markers for example represent the centers, such as the centers of mass, of the 2D markers in space.

After the 2D marker data and the 3D marker data have been obtained, those data can be analyzed. According to the present invention, the relative position between the first camera and the second camera is found by applying a Perspective-n-Points (PnP) algorithm on the 2D marker data and the 3D marker data.

The Perspective-n-Points algorithm finds a virtual position of the first camera relative to the second camera for which the 2D markers at the locations represented by the 3D marker data would result in locations of the 2D markers in the 2D image of the first camera as represented by the 2D marker data. Put differently, the location of a 2D marker in the 2D image in combination with the intrinsic parameters of the first camera defines a line in space, relative to the first camera, on which the 2D marker must lie. Any point on this line is imaged at the corresponding location in the 2D image due to the properties of the first camera. Now a relative position between the cameras has to be found such that the locations of the markers as represented by the 3D marker data lie on the lines in space corresponding to the 2D marker data.

Given a set of 3D points (3 or more) and their corresponding 2D points and the camera matrix (K) of the 2D camera which is used for the 2D points, the Perspective-n-Points algorithm determines the rotation (R) and translation (T) needed in the projection formula of the pin camera model:

$$sp_{2d} = K[R|T]p_{3d}$$

Where all the vectors and matrices are in their homogeneous form (this means with an added dimension having the value of 1 for the vectors, and a row of 0 and 1 for the matrix, wherein the 1 will go in the diagonal position). The camera matrix represents the intrinsic parameters used in the pinhole camera model. It has the focal length of the camera in pixels and the optical center in pixels as well. The camera matrix is parameterized as follows:

$$K = \begin{pmatrix} f_x & sk & x_0 \\ 0 & f_y & y_0 \\ 0 & 0 & 1 \end{pmatrix}$$

In this matrix, $f_x$ and $f_y$ are focal lengths, sk is the axis skew and $x_0$ and $y_0$ represent the principal point offset. Then s is the resulting scale, since the result will be of the form:

$$p_{2d} = \begin{bmatrix} x \\ y \\ w \end{bmatrix} \quad s = \frac{1}{w}$$

And to be homogeneous, w should be equal to 1.

There are several solutions to find the extrinsic parameters ([R|T]) with the Perspective-n-Points algorithms. However, all the variants use the same inputs and will output the Extrinsic parameters (in some cases, an optimized camera matrix as well).

As an example, P3P uses only 3 points to create a system of equations, which will give 4 solutions, and then uses a 4th point to obtain a single solution and discard the rest.

EPnP uses at least 3 points (more points will yield better results in case the data is noisy), to generate several equations based on the sum of 4 weighted control points equal to the data points (4 for the 3D data and 4 for the 2D data), this equations are used to calculate the coefficients needed for the direct calculation of the extrinsic parameters.

In a final example, a system of equations is built out of the equation given before with all the points. Then, using a random or educated guess, it is then refine in an iterative way using gauss newton minimization (minimizing the re-projection error) or Levenberg Marquadt (minimizing the re-projection error as well).

In one embodiment, the method further involves rotating the 3D point cloud such that the planar surface of the phantom, as represented by the rotated 3D point cloud, is perpendicular to the depth direction of the reference system of the second camera, thus obtaining a 2D view of the 3D point cloud. The depth direction for example typically coincides with the optical axis of a ToF camera. It is typically the z axis in the reference system of the second camera. In this context, the expression "2D view" means that all points in the 3D point cloud corresponding to the reflective part of the planar surface have the same depth to the second camera. The 2D view therefore does not comprise spatial deformations caused by the viewing direction of the second camera onto the phantom.

In this embodiment, the method further involves the steps of finding the 2D markers in the 2D view, thus obtaining auxiliary 2D marker data, and of performing an inverse rotation of the auxiliary 2D marker data, thus obtaining the 3D marker data. In the 2D view, the shape of a 2D marker equals the actual physical shape of the 2D marker on the planar surface of the phantom. It is thus easier to find the 2D markers in the 2D view. The inverse rotation is the inverse of the rotation applied to the 3D point cloud to obtain the 2D view. The found locations of the 2D markers in the 2D view are thus transformed back into 3D space, thus forming the locations of the 2D markers in the reference system of the second camera.

In one implementation of this embodiment, a plane is fitted into those points of the 3D point cloud which represent the planar surface of the phantom. Then a transformation is calculated which describes rotations about axes perpendicular to the depth direction of the reference system of the second camera and which makes the plane perpendicular to the depth direction of the reference system of the second camera. This transformation is then applied to the 3D point cloud to obtain the 2D view and the inverse of the transformation is applied to the auxiliary 2D marker data, thus obtaining the 3D marker data. In one example, the points of the 3D point cloud which represent the planar surface of the phantom are points on the reflective part of the planar surface.

In one implementation, the method according to this embodiment involves the step of removing, from the 3D point cloud, those points which do not lie on the plane. This step can be performed before or after the 3D point cloud is rotated. A point is considered as lying on the plane if its distance to the plane is below a threshold, such as the absolute threshold or relative threshold mentioned above in the definition of the word "planar". With this step, the 3D point cloud is basically reduced to points lying on the planar surface.

In one implementation of this embodiment, the 2D view is a depth map of the rotated 3D point cloud. A depth map is a (virtual) 2D image in which the color of each pixel, or the grey value in a grey scale image, represents the distance of a surface point depicted by this pixel from the second camera. In this implementation, points on a reflective part of the planar surface basically have the same color/grey value in the 2D view and points on a non-reflective part of the planar surface have a significantly different color/grey value.

In one implementation of this embodiment, the method for finding the 2D markers in the 2D view is the same as the method for finding the 2D markers in the 2D image. By using the same method (or algorithm), the method becomes more robust, because identical methods are used for obtaining the 2D marker data and the 3D marker data.

In one embodiment, a deviation value of the relative position between the first camera and the second camera is calculated and the steps of capturing a 2D image of the phantom, generating a 3D point cloud, identifying the 2D markers in the 2D image and identifying the 2D markers in the 3D point cloud are repeated if the deviation value is above a predetermined threshold.

With this approach, the confidence of the determined relative position is judged and the process is repeated if this confidence is not high enough.

In one implementation of this embodiment, the 3D marker data is projected into the image plane of the first camera using the relative position between the two cameras found by applying the Perspective-n-Points algorithm and intrinsic parameters of the first camera. In other words, it is simulated at which locations the 2D markers would be in the 2D image, considering the found relative position and the imaging properties of the first camera. Then the distances between the locations of the markers of the projected 3D marker data in the image plane and the locations of the corresponding markers found in the 2D image are calculated and the deviation value is calculated from said distances. In other words, the real locations of the markers in the 2D image are compared to the simulated locations.

In one implementation, the deviation value is the root mean square of the distances, but any other suitable metric can be used.

In one embodiment, the method further involves the step of establishing a one-two-one correspondence between the markers in the 2D marker data and the 3D marker data. This facilitates the application of the Perspective-n-Points algorithm and/or the calculation of the deviation value.

One possible implementation asks for user input which identifies corresponding markers, for example in the 2D image and the 3D point cloud or in the 2D image and the 2D view of the 3D point cloud. The correspondence can also be established automatically. In one example, each marker comprises a unique identification which can be identified both in the 2D image and the 3D point cloud (or the 2D view of the 3D point cloud). The identification can be, for example, any one of a number, a shape or any other code.

In another implementation, the markers in both the 2D image and the 2D view of the 3D point cloud are ordered in a particular order, such as from left to right and from top to bottom. Since the planar surface must be visible to both cameras, the viewing directions of those cameras onto the planar surface are on the same side of the planar surface. The left-to-right arrangement of the markers in the 2D image and the 2D view of the 3D point cloud is therefore identical. It is therefore only possible that the up-down directions of the 2D image and the 2D view of the 3D point cloud are inversed. However, this can typically be disambiguated automatically from the arrangement of the markers.

Another implementation can use prior knowledge about the positions of the markers on the planar surface. This prior knowledge does not have to reflect the exact positions, but only the general arrangement of the markers. In this prior knowledge, every marker can have a unique identification.

As explained above, the present invention makes use of the particular properties of the phantom. The present invention therefore further relates to a medical phantom for use in determining the relative position between a first camera and a second camera, wherein the phantom has a planar surface forming a background on which a plurality of markers are formed. One of the background and the markers is reflective, thus reflecting light emitted by the second camera back to the second camera, and the other one is non-reflective, thus not reflecting light emitted by the second camera back to the second camera.

As explained above, the advantage of such a medical phantom is that the 2D markers cannot only be identified in a 2D image captured by one of the cameras, but also in a 3D point cloud generated by another one of the cameras.

In one embodiment, a reflective area of the planar surface is diffuse reflecting and a non-reflective area of the planar surface is specular reflecting or light absorbing. Regarding details of the medical phantom in general and this embodiment, reference is made to the corresponding passages above.

The present invention further relates to a program which, when running on a computer, causes the computer to perform the method as explained above and/or to a program storage medium on which the program is stored, in particular in a non-transitory form.

The present invention further relates to a computer on which the aforementioned program is stored and/or run.

Still further, the present invention relates to a system comprising a medical phantom as defined above, a first camera, a second camera and a computer as explained above. In one embodiment, the first camera is capable of capturing a 2D image of the phantom and the second camera is capable of generating a 3D point cloud representing points on the surface of the phantom.

In the present invention, the non-reflective part of the planar surface is invisible to the second camera. Compared to markers being holes or 3D salient structures, it is possible to obtain a noiseless marker, which yields more accurate detection results.

In the present invention, the 2D marker data and the 3D marker data are analyzed. Since those marker data represent the same phantom, and therefore the same relative positions of the 2D markers on the planar surface, it is not necessary to know the exact arrangement of the 2D markers on the planar surface, which means that, for example, inaccuracies in the manufacture of the phantom are irrelevant.

Another advantage of the present invention is that is only requires one pair of a 2D image and a 3D point cloud. It is not necessary to capture a plurality of 2D images and/or generate a plurality of 3D point clouds, for example at different points in time or for different positions of the phantom.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The present invention can be used for the applicant's Radiotherapy and Image Guided Surgery devices where it enables a precise positioning and monitoring of patients.

BRIEF DESCRIPTION OF DRAWINGS

In the following, the invention is described with reference to the enclosed figures which represent preferred embodiments of the invention. The scope of the invention is not however limited to the specific features disclosed in the figures, which show.

DETAILED DESCRIPTION

Figure 1:
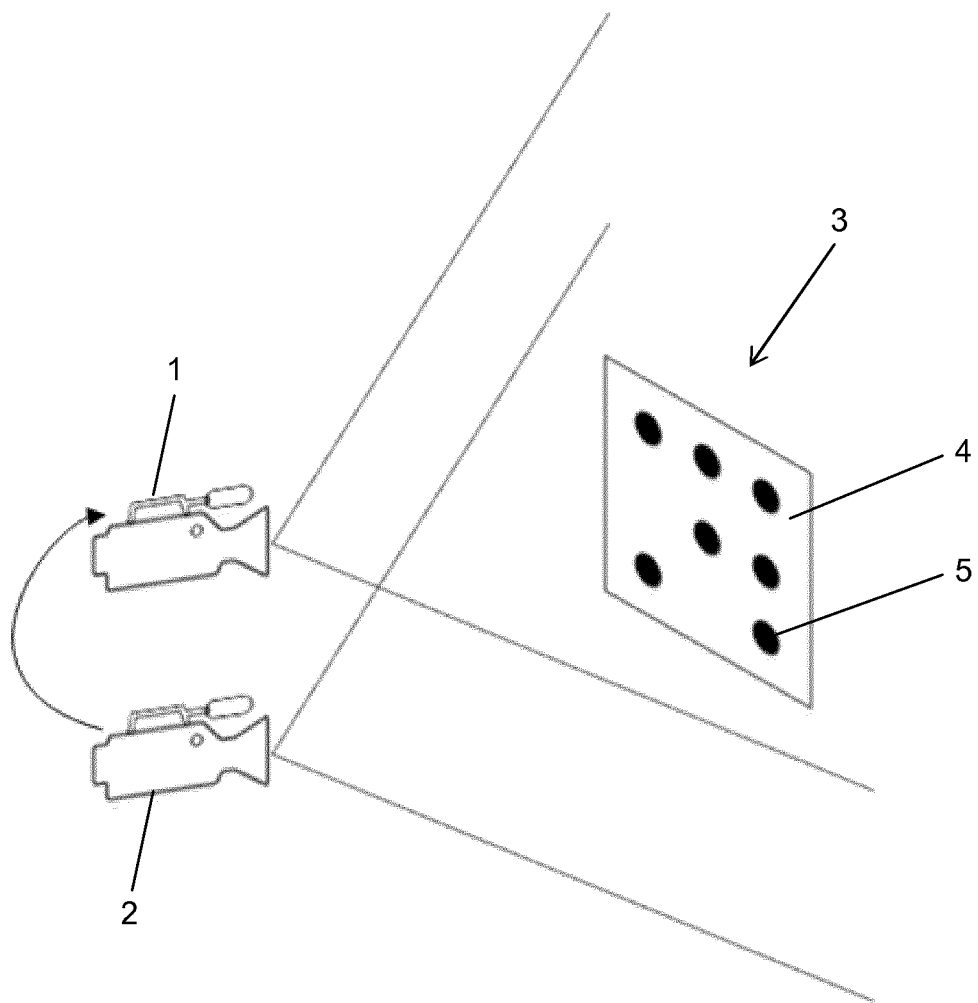
FIG. 1 a setup with two cameras and a phantom,
FIG. 2 a system according to the present invention,
FIG. 3 a flow chart including the present invention,
FIG. 4 a detailed flow chart of analyzing the 3D point cloud, and
FIG. 5 a reduced and transformed version of the 3D point cloud.

FIG. 1 shows a setup of a first camera 1 and a second camera 2. In this exemplary embodiment, the first camera 1 is a camera which can capture 2D images in the visible frequency spectrum. The second camera 2 is a Time-of-Flight (ToF) camera which can generate a 3D point cloud of an object. If the output of both cameras 1 and 2 is to be used in a medical procedure, it is typically essential to know the relative position between the first camera 1 and the second camera 2. This relative position is also referred to as extrinsic parameter of the pair of cameras. It can also be understood as a transformation between the position of the first camera 1 and the second camera 2. It is indicated by the arrow in FIG. 1.

According to the present invention, the relative position between the two cameras 1 and 2 is not determined by tracking markers attached to the cameras. The relative position is rather determined by placing a phantom 3 in the field of view of both cameras and analyzing the output of the two cameras.

In general, the phantom 3 can have any shape. However, it must have a planar surface forming a background 4 on which a plurality of 2D markers 5 are formed. In the present example, the background 4 is reflective, thus reflecting light emitted by the second camera 2 back to the second camera. The markers 5 are non-reflective, thus not reflecting light emitted by the second camera 2 back to the second camera. In the present example, the 2D markers 5 are circular. However, they can have any other suitable shape.

The markers 5 can, for example, be formed by applying a non-reflective paint, a non-reflective coating, a non-reflective foil or a non-reflective sticker.

The background 4 has a geometric size in terms of a surface area. The background 4, and therefore the planar surface, is considered to be planar if the distance of the points on the surface from a plane fitted into those points is small compared to the surface area of the planar surface, and is, for example, smaller than $1/50$ or $1/100$ of the square root of the size of the planar surface/background 4.

Figure 2:
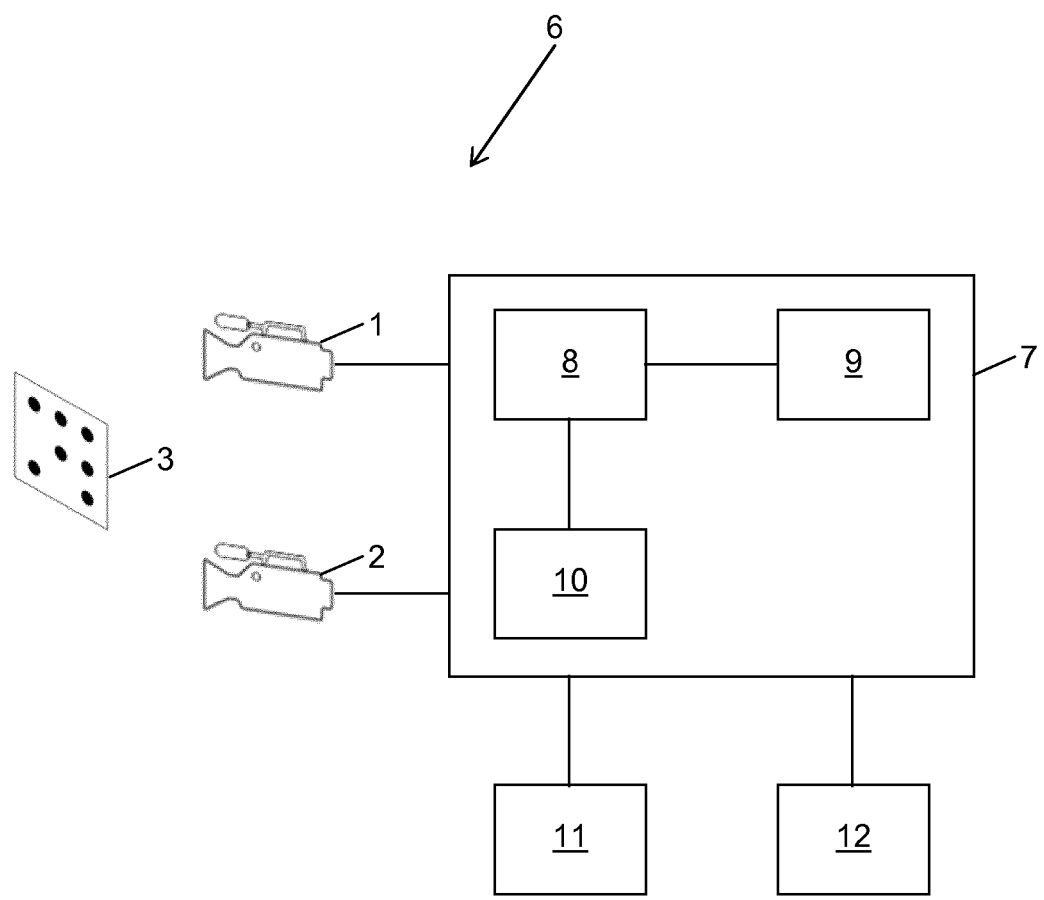

FIG. 2 shows a system 6 according to the present invention. The system 6 comprises the first camera 1, the second camera 2, the phantom 3 and a computer 7, which is connected to an optional input device 11 and an optional output device 12. The input device 11 is, for example, a keyboard, a mouse or a touch sensitive surface. The output device 12 is, for example, a monitor.

The computer 7 comprises a central processing unit (CPU) 8, a memory unit 9 and an interface 10. Via the interface 10, the computer 7 is connected to the first camera 1 and the second camera 2.

The memory unit 9 stores program data comprising instructions for the CPU 8 such that it performs the data processing according to the present invention. It further stores data to be processed, such as the 2D image captured by the first camera 1 and the 3D point cloud generated by the second camera 2, and processed data.

Figure 3:
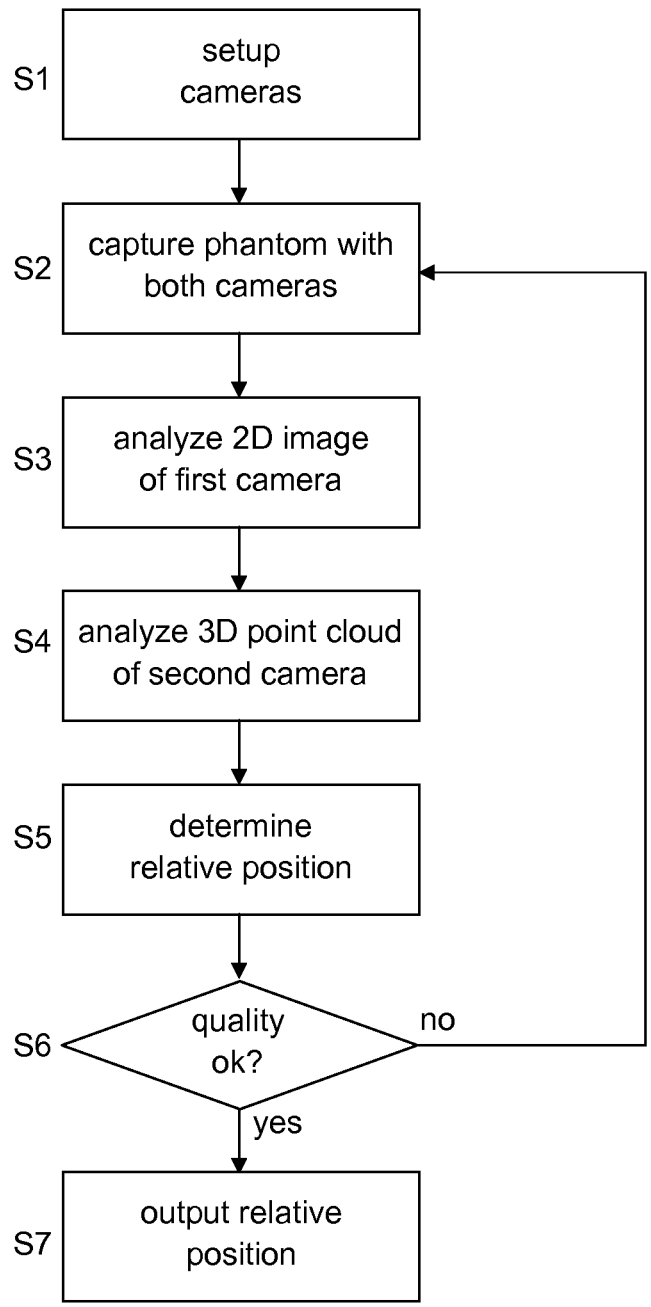

FIG. 3 shows a flowchart of a method including the present invention.

In step S1, the cameras 1 and 2 are set up. This means that the cameras are positioned as required for the medical procedure to be performed. Once step S1 has been performed, the method of the present invention can be carried out.

In step S2, the phantom 3 is captured by both the first camera 1 and the second camera 2. This means that the first camera 1 captures a 2D image of the phantom 3 and the second camera 2 generates a 3D point cloud representing points on the surface of the phantom 3. In particular, a light source of the second camera 2 emits light onto the phantom 3 and analyzes the run time of the reflected light to determine distances of points on the phantom 3. The second camera typically generates the 3D point cloud as a set of 3D coordinates in the reference system of the second camera. The 3D coordinates are typically x, y and z coordinates, wherein the z coordinate represents a depth direction of the second camera 2. The x, y and z axes constitute an orthogonal coordinate system.

In step S3, the 2D image captured by the first camera 1 is analyzed. This means that the 2D markers are identified in the 2D image. Identifying a marker in the 2D image means determining the location of the 2D marker, in particular of the center of the 2D marker, in the 2D image. The locations of all identified 2D markers are then commonly referred to as 2D marker data. Due to the intrinsic parameters of the first camera 1, every location of a marker in the 2D image has an associated line in space on which the corresponding marker lies. This line in space is defined with respect to the first camera 1.

In step S4, the 3D point cloud generated by the second camera is analyzed. This means that the 2D markers are identified in the 3D point cloud. Identifying a marker in the 3D point cloud means finding the location of the 2D marker, in particular of the center of the 2D marker, in space, defined in a reference system of the second camera 2. Step S4 results in 3D marker data representing the locations of the found 2D markers, for example in terms of a set of three-dimensional coordinates. Details of step S4 will be explained later.

In step S5, the relative position between the first camera 1 and the second camera 2 is determined. This is achieved by applying a Perspective-n-Points algorithm on the 2D marker data and the 3D marker data. The Perspective-n-Points algorithm finds a position of the first camera 1 relative to the second camera 2 such that simulated locations of the 2D markers in a simulated 2D image match the locations represented by the 2D marker data, either exactly or as closely as possible. The simulated locations are calculated by projecting the locations of the 2D markers as represented by the 3D marker data into the image plane of the first camera 1, considering an assumed relative position and the intrinsic parameters of the first camera 1.

The relative position between the cameras 1 and 2 defines the positions of the lines corresponding to the 2D marker data in the reference system of the camera 2. The PnP algorithm finds a relative position such that the locations defined by the 3D marker data lie on those lines. This is facilitated by the optional step of establishing a one-to-one correspondence of the markers found in the 2D image and the 3D point cloud, which means a one-to-one correspondence between every location in the 2D marker data with a location in the 3D marker data. It is then known which location in the 3D marker data must lie on which line corresponding to the 2D marker data.

In step S6, it is determined whether or not the quality of the found relative position is sufficient, which means that the deviation of the found relative position between the first camera 1 and the second camera 2 and the correct relative position is below a predetermined threshold. A suitable metric is the root mean square of the pair-wise distances between the locations represented by the 2D marker data and the corresponding virtual locations explained above. The found relative position is good enough if this root mean square is below a predetermined threshold.

If the quality is not good enough, then the process returns to step S2, where the phantom 3 is captured again using both the first camera 1 and the second camera 2. Steps S3 to S5 are then repeated with the new 2D image and the new 3D point cloud.

If it is determined in step S6 that the quality is good enough, then the relative position is output in step S7, for example to a computer or a software which analyzes the output of the first camera 1 and/or the second camera 2 during a medical procedure.

Figure 4:
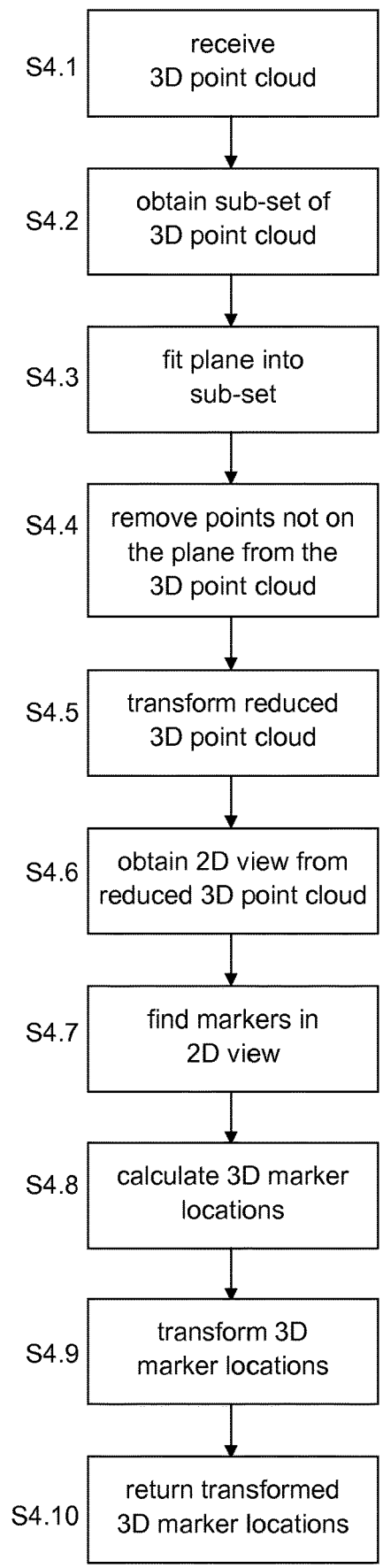

FIG. 4 shows a detailed flowchart of the step S4 of analyzing the 3D point cloud in FIG. 3.

In step S4.1, the 3D point cloud is received.

In step S4.2, a sub-set of the 3D point cloud is obtained. The sub-set of the 3D point cloud only comprises points lying on the planar surface of the phantom 3, which means points on the background 4 and/or points on the markers 5. However, it is not necessary that the sub-set contains all points on the planar surface.

One implementation of step S4.2 assumes that the phantom 3, and thus its planar surface, is placed in a predetermined location relative to the second camera 2. Points on the planar surface then lie in a predetermined range of the x and y coordinates of the reference system of the second camera 2. Points in this range then constitute the sub-set of the 3D point cloud.

It is further possible to optionally grow this sub-set by adding neighboring points of the 3D cloud which lie in the plane defined by the points within said range. A point might be considered as lying in the plane if its distance to the plane is below a predetermined threshold as explained with reference to step S4.4 below.

The background 4 of the phantom 3 might have a boundary around it which has the same property (reflective or non-reflective) as the markers 5. The growth of the sub-set can be stopped if this boundary is reached.

In step S4.3, a plane is fitted into the sub-set of the 3D point cloud obtained in step S4.2. In addition, the orientation of a normal to the found plane is calculated. Any suitable algorithm for fitting a plane into a set of points can be used.

In step S4.4, points which do not lie in the plane are removed from the original 3D point cloud. It shall be noted that not only points which lie exactly in the plane are maintained in the 3D point cloud, but also points with a distance to the plane which is below a certain threshold. This threshold can be an absolute threshold, such as 1 mm, 2 mm, 3 mm, 4 mm or 5 mm. The threshold can also be a relative threshold which is defined in relation to the size of the planar surface, for example the square root of the size of the planar surface. The result of step S4.4 is a reduced 3D point cloud.

In step S4.5, the reduced 3D point cloud is transformed, in particular rotated. In particular, the reduced 3D point cloud is transformed such that the normal to the plane found in step S4.3 is parallel to the z-axis of the reference system of the second camera 2. In the case of a ToF camera as the second camera 2, the x- and y-axes of the camera's reference system lie in the image plane of the ToF camera and the z-axis is perpendicular thereto. With the transformation performed in step S4.5, all points in the reduced 3D point cloud have basically or exactly the same distance to the second camera 2.

Figure 5:
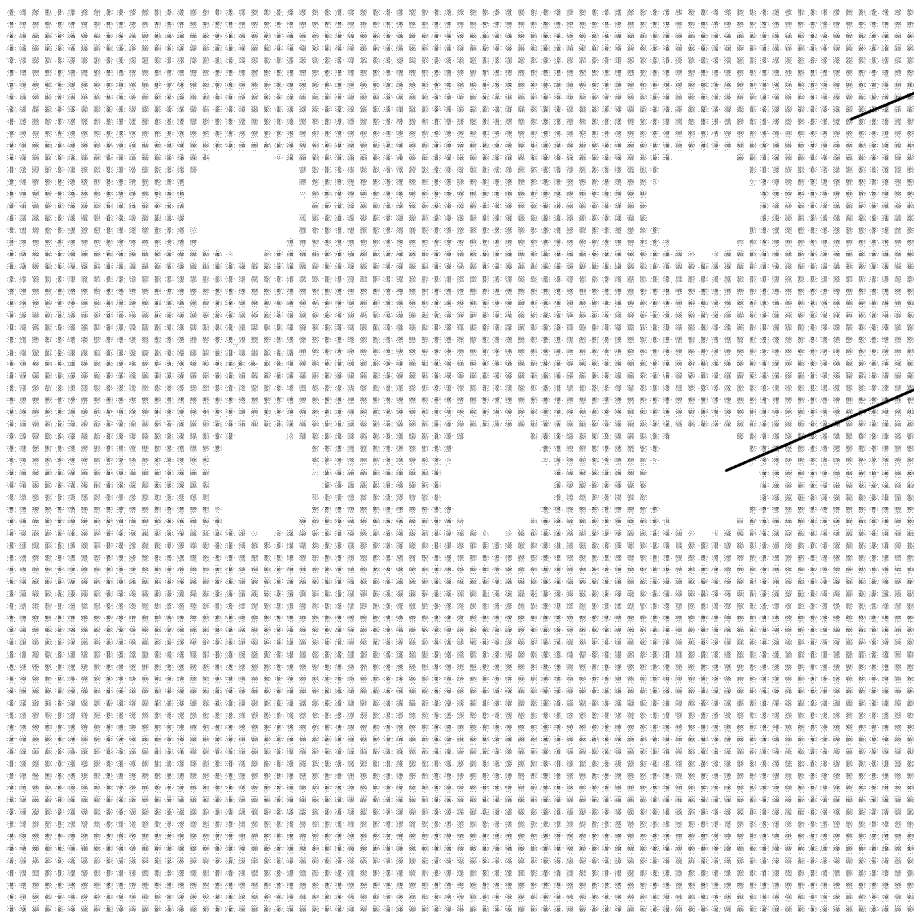

FIG. 5 shows an example of a reduced and transformed 3D point cloud. There are only points corresponding to the background 4 of the planar surface. At the locations of the markers 5 on the planar surface, there are no points in the reduced and transformed version of the 3D point cloud because the 2D markers have not reflected light back to the second camera 2.

In step S4.6, a 2D view is obtained from the reduced and transformed 3D point cloud. The 2D view is, for example, a 2D grey-scale image, wherein the grey value of a pixel is determined from one or more corresponding points in the reduced and transformed 3D point cloud. This means mapping the 3D coordinates of the points in the reduced and transformed 3D point cloud into 2D coordinates in the 2D view and a grey value.

Since all points of the reduced and transformed 3D point cloud have (basically) the same distance to the second camera 2, the corresponding pixels in the 2D view have the same or almost the same grey value. However, pixels corresponding to the markers 5 are either black or white, depending on the mapping of the distance to the grey values. The 2D view can also be binarized, such that pixels corresponding to the background 4 are white and pixels corresponding to the markers 5 are black, or vice versa.

The markers are then identified in the 2D view in step S4.7. The same algorithm as in step S3 can be used. The results of step S4.7 are the locations of the markers, in particular of the centers of the markers, in the image plane of the 2D view.

In step S4.8, the locations of the markers found in step S4.7 are transformed into 3D marker locations. This involves an inverse mapping to the mapping performed in step S4.6. In particular, the 2D coordinate of a location is mapped to the x and y coordinates in the reference system of the second camera. The z coordinate for example corresponds to the z coordinate of one of the points in the reduced and transformed 3D point cloud or the average of the z coordinates of two or more points in the reduced and transformed 3D point cloud.

The 3D marker locations resulting from step S4.8 represent the centers of the "holes" in the reduced and transformed 3D point cloud. In step S4.9, those 3D marker locations are transformed using the inverse of the transform used in step S4.5. This means that the 3D marker locations are transformed to the original position of the 3D point cloud relative to the second camera 2. In step S4.10, the transformed 3D marker positions are returned as the 3D marker data.

As outlined above, the present invention makes use of the finding that non-reflective areas are invisible to the second camera 2. This means that the generated 3D point cloud does not comprise points corresponding to non-reflective parts of the surface of the phantom 3. This allows identifying the markers even in the 3D point cloud.

The invention claimed is:

1. A method for determining the relative position between a first camera and a second camera used in a medical application,
wherein the first camera captures a 2D image of a phantom, the second camera emits light onto the phantom and analyzes the reflected light, generating a 3D point cloud representing points on a surface of the phantom wherein the phantom has a planar surface forming a background on which a plurality of 2D markers are formed,
wherein one of the background and the 2D markers is reflective reflecting light emitted by the second camera back to the second camera and the other one of the background and the 2D markers is non-reflective thus not reflecting light emitted by the second camera back to the second camera; wherein the determining the relative position between the first camera and the second camera comprises the following steps:
capturing by the first camera a 2D image of the phantom;
generating by the second camera a 3D point cloud representing the planar surface of the phantom;
identifying the 2D markers in the 2D image thus obtaining 2D marker data representing the locations of the 2D markers in the 2D image;
identifying the 2D markers in the 3D point cloud and obtaining 3D marker data representing the locations of the 2D markers in a reference system of the second camera, and
determining the relative position between the first camera and the second camera by applying a Perspective-n-Points algorithm to the 2D marker data and the 3D marker data;
wherein identifying the 2D markers in the 3D point cloud includes:
rotating the 3D point cloud such that the planar surface of the phantom is perpendicular to a depth direction of the reference system of the second camera, thus obtaining a 2D view of the 3D point cloud;
locating the 2D markers in the 2D view obtaining auxiliary 2D marker data and performing an inverse rotation of the auxiliary 2D marker data obtaining the 3D marker data; and
performing an inverse rotation of the auxiliary 2D marker data, wherein a plane is fitted into the points of the 3D point cloud which represent the planar surface of the phantom, a transformation describing rotations about axes perpendicular to the depth direction of the reference system of the second camera and making the plane perpendicular to said depth direction is calculated, the transformation is applied to the 3D point cloud and the inverse of the transformation is applied to the auxiliary 2D marker data.

2. The method of claim 1 wherein the identifying the 2D markers in the 3D point cloud uses the property that points on a non-reflective part of the planar surface are identified as having a larger distance to the second camera than points on the reflective part of the planar surface.

3. The method of claim 1 wherein the Perspective-n-Points algorithm includes providing a reference system of the first camera; finding a transformation which transforms the 3D marker data from the reference system for the second camera into the reference system for the first camera such that all transformed locations of the 2D markers as represented by the transformed 3D marker data lie on lines in the reference system of the first camera corresponding to the 2D marker data.

4. The method of claim 1 wherein the determining the relative position between the first camera and the second camera includes defining a first reference system for the first camera and a second reference system for the second camera and finding a transformation which transforms the 3D marker data from the second reference system into the first reference system such that all transformed locations of the 2D markers as represented by the transformed 3D marker data lie on lines in the first reference system corresponding to the 2D marker data.

5. The method of claim 1 wherein the determining the relative position between the first camera and the second camera involves:
transforming the 3D marker data into the reference system of the first camera using a transformation,
projecting the transformed 3D marker data into the image plane of the first camera,
comparing the projected transformed 3D marker data with the 2D marker data,
wherein when the projected transformed 3D marker data substantially correspond to the 2D marker data, the transformation corresponds to the relative position between the first camera and the second camera, and
obtaining the relative position between the first camera and the second camera from the transformation.

6. The method of claim 1, wherein points of the 3D point cloud which do not lie on the plane are removed from the 3D point cloud.

7. The method of claim 1, wherein the 2D view is a depth map of the rotated 3D point cloud.

8. The method of claim 1, wherein the method for finding the 2D markers in the 2D view is the same as the method for finding the 2D markers in the 2D image.

9. The method of claim 1, wherein a deviation value of the relative position between the first camera and the second camera is calculated and wherein the determining the relative position between the first camera and the second camera is repeated if the deviation value is above a predetermined threshold.

10. The method of claim 9, wherein the 3D marker data is projected into the image plane of the first camera using the determined relative position and intrinsic parameters of the first camera, the distances between the locations of the markers of the projected 3D marker data in the image plane and the locations of the corresponding markers found in the 2D image are calculated and the deviation value is calculated from the said distances.

11. The method of claim 10, wherein the deviation value is the root mean square of the distances.

12. The method of claim 1, wherein a one-to-one correspondence between the markers in the 2D marker data and the 3D marker data is established.

13. The method of claim 1 wherein the phantom has a planar surface forming a background on which a plurality of 2D markers are formed.

14. The method of claim 13 wherein the phantom includes a reflective area of the planar surface which is diffuse reflecting and a non-reflective area of the planar surface is specular reflecting or light absorbing.

15. A non-transitory computer readable storage medium storing computer instructions executable by one or more processors to perform a method comprising:
    capturing by a first camera a 2D image of a phantom which has a planar surface forming a background on which a plurality of 2D markers are formed;
    generating by a second camera a 3D point cloud representing the planar surface of the phantom;
    identifying the 2D markers in the 2D image thus obtaining 2D marker data representing the locations of the 2D markers in the 2D image;
    identifying the 2D markers in the 3D point cloud and obtaining 3D marker data representing the locations of the 2D markers in a reference system of the second camera, and
    determining the relative position between the first camera and the second camera by applying a Perspective-n-Points algorithm to the 2D marker data and the 3D marker data;
    wherein identifying the 2D markers in the 3D point cloud includes:
    rotating the 3D point cloud such that the planar surface of the phantom is perpendicular to a depth direction of the reference system of the second camera, thus obtaining a 2D view of the 3D point cloud;
    locating the 2D markers in the 2D view obtaining auxiliary 2D marker data and performing an inverse rotation of the auxiliary 2D marker data obtaining the 3D marker data; and
    performing an inverse rotation of the auxiliary 2D marker data, wherein a plane is fitted into the points of the 3D point cloud which represent the planar surface of the phantom, a transformation describing rotations about axes perpendicular to the depth direction of the reference system of the second camera and making the plane perpendicular to said depth direction is calculated, the transformation is applied to the 3D point cloud and the inverse of the transformation is applied to the auxiliary 2D marker data.

16. A system for determining the relative position between a first camera and a second camera used in a medical application, comprising:
    at least one computer having at least one processor connected to memory, the memory having instructions stored thereon,
    wherein the first camera captures a 2D image of a phantom, the second camera emits light onto the phantom and analyzes the reflected light, generating a 3D point cloud representing points on a surface of the phantom wherein the phantom has a planar surface forming a background on which a plurality of 2D markers are formed,
    wherein one of the background and the 2D markers is reflective reflecting light emitted by the second camera back to the second camera and the other one of the background and the 2D markers is non-reflective thus not reflecting light emitted by the second camera back to the second camera;
    wherein the determining the relative position between the first camera and the second camera includes executing instructions by the at least one processor to:
    capture by the first camera the 2D image of the phantom;
    generate by the second camera the 3D point cloud representing the planar surface of the phantom;
    identify the 2D markers in the 2D image thus obtaining 2D marker data representing the locations of the 2D markers in the 2D image;
    identify the 2D markers in the 3D point cloud and obtaining 3D marker data representing the locations of the 2D markers in a reference system of the second camera, and
    determine the relative position between the first camera and the second camera by applying a Perspective-n-Points algorithm to the 2D marker data and the 3D marker data;
    wherein identifying the 2D markers in the 3D point cloud includes:
    rotate the 3D point cloud such that the planar surface of the phantom is perpendicular to a depth direction of the reference system of the second camera, thus obtaining a 2D view of the 3D point cloud;
    locate the 2D markers in the 2D view obtaining auxiliary 2D marker data and performing an inverse rotation of the auxiliary 2D marker data obtaining the 3D marker data; and
    perform an inverse rotation of the auxiliary 2D marker data, wherein a plane is fitted into the points of the 3D point cloud which represent the planar surface of the phantom, a transformation describing rotations about axes perpendicular to the depth direction of the reference system of the second camera and making the plane perpendicular to said depth direction is calculated, the transformation is applied to the 3D point cloud and the inverse of the transformation is applied to the auxiliary 2D marker data.

* * * * *